United States Patent
Swan et al.

(10) Patent No.: US 10,398,310 B2
(45) Date of Patent: Sep. 3, 2019

(54) OPHTHALMOSCOPES

(71) Applicant: Optos PLC, Dunfermline, Scotland (GB)

(72) Inventors: Derek Swan, Dunfermline (GB); Gonzalo Muyo, Dunfermline (GB); Alistair Gorman, Dunfermline (GB)

(73) Assignee: Optos PLC, Dunfermline (GB)

( * ) Notice: Subject to any disclaimer, the term of this patent is extended or adjusted under 35 U.S.C. 154(b) by 3 days.

(21) Appl. No.: 15/325,020

(22) PCT Filed: Jul. 10, 2015

(86) PCT No.: PCT/GB2015/052001
§ 371 (c)(1),
(2) Date: Jan. 9, 2017

(87) PCT Pub. No.: WO2016/005763
PCT Pub. Date: Jan. 14, 2016

(65) Prior Publication Data
US 2017/0202457 A1   Jul. 20, 2017

(30) Foreign Application Priority Data

Jul. 10, 2014   (GB) .................................. 1412269.1

(51) Int. Cl.
*A61B 3/10* (2006.01)
*A61B 3/12* (2006.01)
*G02B 26/10* (2006.01)

(52) U.S. Cl.
CPC .............. *A61B 3/12* (2013.01); *A61B 3/1025* (2013.01); *G02B 26/105* (2013.01)

(58) Field of Classification Search
CPC ......... A61B 3/1225; A61B 3/12; A61B 3/103; A61B 3/1015; A61B 3/1025;
(Continued)

(56) References Cited

U.S. PATENT DOCUMENTS 5,202,711 A    4/1993 Klingbeil
6,337,920 B1 *  1/2002 Muhlhoff ............. A61B 3/1225
                                              351/200
(Continued)

FOREIGN PATENT DOCUMENTS

CN        101136504 A    3/2008
CN        102365573 A    2/2012
(Continued)

OTHER PUBLICATIONS

International Search Report for International Application No. PCT/GB2015/052001 dated Oct. 28, 2015.
(Continued)

*Primary Examiner* — William R Alexander
*Assistant Examiner* — Henry A Duong
(74) *Attorney, Agent, or Firm* — Pavan K. Agarwal; Shabbi S. Khan; Foley & Lardner LP (57) ABSTRACT

An ophthalmoscope (1) and method for scanning a fundus (23) of an eye (9), comprising a light system (3) which produces linear light, a scanner (5) which receives at least some of the linear light and is movable about a scan axis to produce a 1D scan of the at least some linear light, and a scan transfer system (7) which receives the 1D scan from the scanner and transfers the 1D scan to the eye, wherein the scanner is positioned in the ophthalmoscope such that it receives the at least some of the linear light substantially along the scan axis, the scan transfer system positioned in the ophthalmoscope such that a pupil of the eye is provided at a focal point of the system, and the scanner is positioned in the ophthalmoscope and the scan transfer system is configured to transfer the 1D scan from the scanner through the focal point at the eye pupil and onto the eye fundus.

39 Claims, 5 Drawing Sheets

(58) Field of Classification Search
CPC ... A61B 3/0008; A61B 3/1233; A61B 3/1241; G02B 26/105
USPC ........................................................ 351/221
See application file for complete search history.

(56) References Cited

U.S. PATENT DOCUMENTS

2003/0231285 A1    12/2003  Ferguson
2013/0176535 A1*    7/2013  Mensink .............. A61B 3/1025
                                              351/221

FOREIGN PATENT DOCUMENTS

| CN | 103108582 | 5/2013 |
| GB | 2 440 163 A | 1/2008 |
| GB | 2 498 855 | 7/2013 |
| JP | H09-131322 | 5/1997 |
| WO | WO-2011/135348 A2 | 11/2011 |
| WO | WO-2014/053824 | 4/2014 |

OTHER PUBLICATIONS

Search Report for GB 1412269.1 dated Jan. 28, 2015.
Summary of Office Action on Chinese Application No. 2015800416880.
Office Action on Japanese Application No. 2017-501223 dated Jan. 29, 2019.
Summary of Office Action on Chinese Application No. 2015800416880 dated Apr. 4, 2019.

* cited by examiner

OPHTHALMOSCOPES

TECHNICAL FIELD

The invention relates to ophthalmoscopes and particularly improvements in the operation and layout of ophthalmoscopes.

BACKGROUND OF THE INVENTION

Numerous types of ophthalmoscopes exist. In some of these, the choice of components to achieve advantages such as ultra wide field imaging of a fundus of an eye, introduces problems such as aberration and the necessity for large scale optical systems. Aberration can lead to deterioration of the point spread function of both the input illumination relayed to the eye and the return illumination from the eye. This, in turn, can lead to a loss of image resolution and a loss of return illumination as a function of the field of view. Large scale optical systems are required in order to avoid patient features clashing with input beams etc. which increases the manufacturing complexity, and therefore cost, of the ophthalmoscopes.

BRIEF SUMMARY OF THE INVENTION

According to a first aspect of the invention there is provided an ophthalmoscope for scanning a fundus of an eye, comprising
  a light system which produces linear light,
  a scanner which receives at least some of the linear light and is movable about a scan axis to produce a 1D scan of the at least some linear light, and
  a scan transfer system which receives the 1D scan from the scanner and transfers the 1D scan to the eye,
wherein the scanner is positioned in the ophthalmoscope such that it receives the at least some of the linear light substantially along the scan axis, the scan transfer system is positioned in the ophthalmoscope such that a pupil of the eye is provided at a focal point of the system, and the scanner is positioned in the ophthalmoscope and the scan transfer system is configured to transfer the 1D scan from the scanner through the focal point at the eye pupil and onto the eye fundus.

The scanner may be positioned in the ophthalmoscope such that it receives the at least some of the linear light with a central axis of the light substantially coincidental with the scan axis.

The scanner may have a shape such that a scan direction of the 1D scan of the linear light lies at an angle to the scan axis of the scanner. The scanner shape may be substantially flat and the angle may be approximately 90 degrees.

The scanner may comprise a reflective element. The reflective element may comprise a mirror. The scanner may be driven by, for example, a motor to move it about the scan axis. The scanner may have dimensions such that it receives substantially all of the linear light produced by the light system. The scanner may have dimensions such that it receives substantially all of return light from the eye fundus.

The scan transfer system may comprise a scan transfer component. The scan transfer system may be configured to transfer the 1D scan from the scanner through the focal point at the eye pupil and onto the eye fundus by election of a shape of the scan transfer component. The scan transfer component may have an aspherical shape. The scan transfer component may have a shape of a section of a conical surface. The shape of the section of the conical surface may be any of parabolic, ellipsoidal, hyperboloid.

The scan transfer component may comprise a reflective component. The reflective component may have a shape described by one or more polynomial functions of two variables, for example, two variables describing substantially orthogonal axes of the reflective component. The reflective component may comprise a mirror.

The scan transfer component may comprise a transmissive component. The transmissive component may comprise a lens.

The scan transfer component may have a shape such that the at least some linear light of the 1D scan is collimated at a location adjacent an outer surface of a cornea of the eye. The collimated light at the eye cornea is then focussed by the eye cornea and lens to give light having an optimised spread function at substantially each of a plurality of positions of a scan field on the eye fundus.

The scan transfer component may have a shape such that return light from substantially each of a plurality of positions of the scan field on the eye fundus has substantially similar focal properties and is substantially brought to a focus on a plane. A standard confocal aperture may then be used to optimise the signal-to-noise of the fundus return light over, for example, corneal return light.

The scan transfer component may have dimensions such that it receives substantially all of the 1D scan from the scanner. The scan transfer component may have dimensions such that it receives substantially all of return light from the eye fundus. Thus the scan transfer component is able to collect light exiting the eye at wide and ultra wide angles, providing a wide and ultra wide ophthalmoscope.

The scan transfer system may comprise a plurality of scan transfer components. The scan transfer system may be configured to transfer the 1D scan from the scanner through the focal point at the eye pupil and onto the eye fundus by election of shapes of the scan transfer components and positions of the scan transfer components. The scan transfer components may each have an aspherical shape. The scan transfer components may each have a shape of a section of a conical surface. The shape of the section of the conical surface may any of parabolic, ellipsoidal, hyperboloid, alone or in combination.

The scan transfer components may each comprise a reflective component. At least some of the reflective components may have a shape described by one or more polynomial functions of two variables, for example, two variables describing substantially orthogonal axes of the reflective component. The reflective components may each comprise a mirror.

The scan transfer components may each comprise a transmissive component. The transmissive components may each comprise a lens.

The scan transfer components may each have a shape such that the at least some linear light of the 1D scan is collimated at a location adjacent an outer surface of a cornea of the eye. The collimated light at the eye cornea is then focussed by the eye cornea and lens to give light having an optimised spread function at substantially each of a plurality of positions of a scan field on the eye fundus.

The scan transfer components may each have a shape such that return light from substantially each of a plurality of positions of the scan field on the eye fundus has substantially similar focal properties and is substantially brought to a focus on a plane. A standard confocal aperture may then be used to optimise the signal-to-noise of the fundus return light over, for example, corneal return light.

The scan transfer components may each have dimensions such that they receive substantially all of the 1D scan from the scanner. The scan transfer components may each have dimensions such that they receive substantially all of return light from the eye fundus. Thus the scan transfer components are able to collect light exiting the eye at wide and ultra wide angles, providing a wide and ultra wide ophthalmoscope.

The light system may comprise a point source of light and a scan device which receives the point light and is movable about a scan axis to scan the point light to produce the linear light. The linear light may comprise a plurality of rays of light which are produced consecutively by the scan device scanning the point light and which fall on a line at the scanner.

The scan device may be positioned in the ophthalmoscope such that it receives the point light substantially on the scan axis. The scan device may be positioned in the ophthalmoscope such that the scan axis lies in a plane conjugate to the eye pupil. Light incident on the scan axis will then be focussed at and pass through the eye pupil.

The scan device may be positioned in the ophthalmoscope such that the scan axis of the scan device lies at an angle to the scan axis of the scanner. The angle may be approximately 90 degrees. The scan device may comprise a plane mirror. The scan device may be driven by, for example, a motor to move it about the scan axis.

The light system may comprise a point source of light and a light line generator to produce the linear light. The linear light may comprise a plurality of rays of light which are produced simultaneously by the light line generator and which form a line of light at the scanner. The light line generator may comprise, for example, beam shaping optics such as wedge-like cylindrical lenses, or diffractive optical elements that transform Gaussian point light into top-hat linear light.

The light system may comprise a linear array of point sources of light to produce the linear light. The linear light may comprise a plurality of rays of light which are produced simultaneously by the point sources of light and which form a line of light at the scanner.

The or each point source of light may comprise a laser or a light emitting diode (LED).

The ophthalmoscope may comprise a scan transfer device. The scan transfer device may be positioned in the ophthalmoscope between the light system and the scanner to relay the at least some linear light from the light system to the scanner. The scan transfer device may comprise an aspheric mirror. The scan transfer device may have a shape such that aberration in the ophthalmoscope is decreased. The scan transfer device may be positioned in the ophthalmoscope such that aberration in the ophthalmoscope is decreased. The scan transfer device thus extends the degrees of freedom in the design of the ophthalmoscope by providing a further means of controlling the aberration and scan angles onto the fundus.

The ophthalmoscope may be a wide field ophthalmoscope. The ophthalmoscope may be an ultra-wide field ophthalmoscope. The ophthalmoscope may operate in a reflectance mode. The ophthalmoscope may operate in a fluorescence mode. The ophthalmoscope may be used for optical coherence tomography.

Where reference is made to the fundus of an eye, it is to be understood that this includes, but is not limited to, the retina, optic disc, macula, fovea, posterior pole, Bruch's membrane and choroid of the eye.

The ophthalmoscope of the invention provides a number of advantages over previous ophthalmoscopes. The advantages are realised by a combination of the chosen shape and positioning of the components of the ophthalmoscope. For example, appropriate selection of particularly the shape of the component or components of the scan transfer system and the positioning of the scanner allows aberration in the ophthalmoscope to be decreased. This, in turn, allows the ophthalmoscope to obtain high resolution, confocal scanning of the fundus. Previous ophthalmoscopes have used a ellipsoidal scan transfer device and have placed the scanner at a first focal point of the device and the eye at a second focal point of the device, resulting in the scanner having to be in line with the eye. In not using this arrangement, the ophthalmoscope of the invention has more degrees of freedom in the choice of shape and positioning of its components. This allows the ophthalmoscope of the invention to use a more compact optical arrangement, achieving a significant reduction of the overall size of the ophthalmoscope. In particular, as the scanner no longer has to be in line with the eye, the size and therefore the cost of the scan transfer system can be reduced.

According to a second aspect of the invention there is provided a method of scanning a fundus of an eye, comprising
  using a light system to produce linear light,
  using a scanner to receive at least some of the linear light, the scanner being positioned in the ophthalmoscope to receive the at least some of the linear light substantially along a scan axis of the scanner,
  moving the scanner about the scan axis to produce a 1D scan of the at least some of the linear light, the scanner being positioned in the ophthalmoscope to transfer the 1D scan from the scanner through a pupil of the eye and onto the eye fundus, and
  using a scan transfer system to receive the 1D scan from the scanner and transfer the 1D scan to the eye, the scan transfer system being positioned in the ophthalmoscope to provide the eye pupil at a focal point of the system and the scan transfer system being configured to transfer the 1D scan from the scanner through the focal point at the eye pupil and onto the eye fundus.

BRIEF DESCRIPTION OF THE DRAWINGS

Embodiments of the invention will now be described by way of example only, with reference to the accompanying drawings, in which.

DETAILED DESCRIPTION OF THE INVENTION

Figure 1:
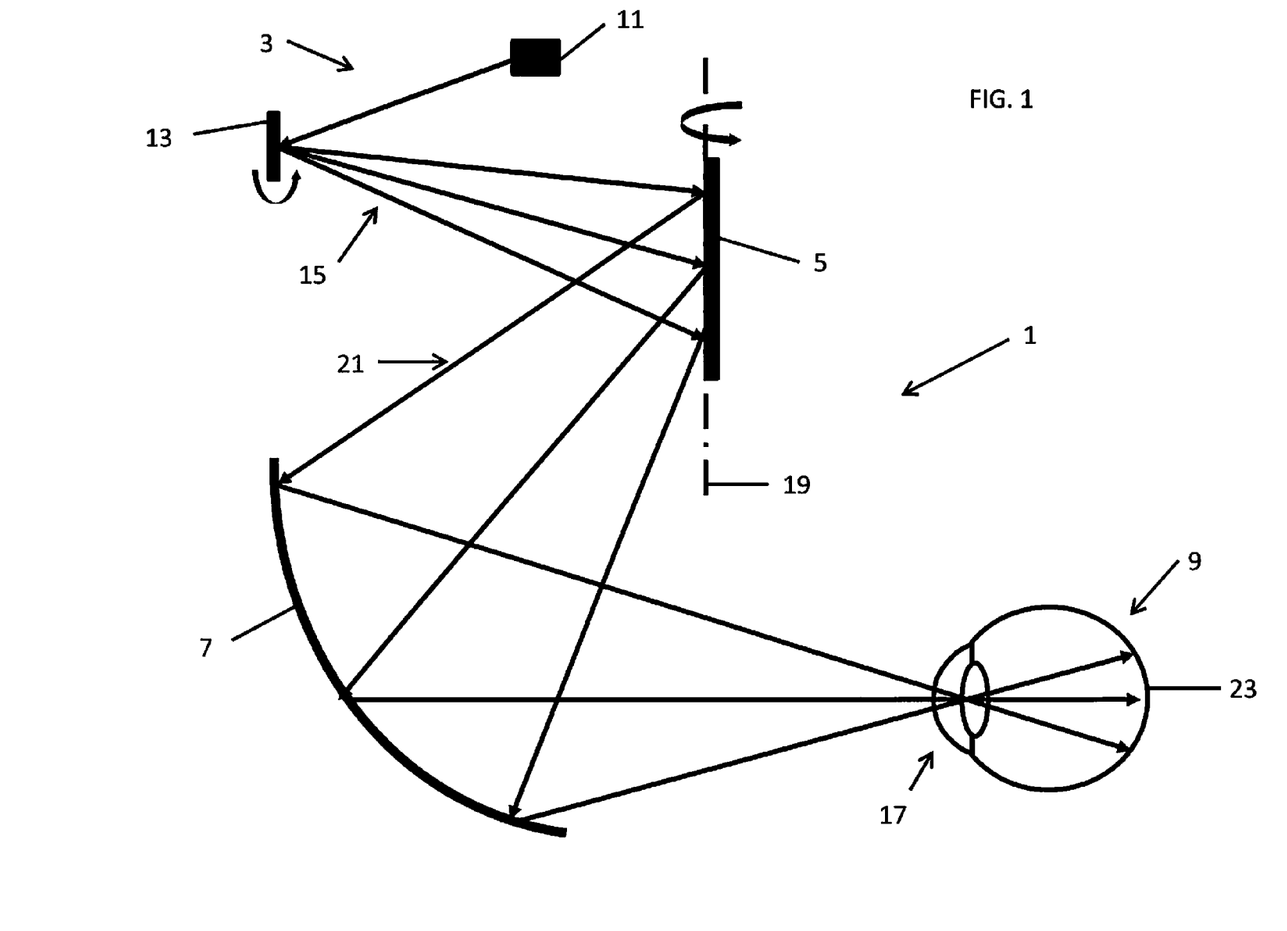
FIG. 1 is a schematic representation of a first embodiment of the ophthalmoscope according to the first aspect of the invention.

Referring to FIG. 1, a first embodiment of an ophthalmoscope according to the invention is shown. The ophthalmoscope 1 comprises a light system 3, a scanner 5 and a scan transfer system 7 and is used in scanning an eye 9.

The light system 3 comprises a point source of light 11, comprising a laser, and a scan device 13, comprising a plane mirror. The scan device 13 receives point light from the source 11 and is driven by a motor (not shown) to move the device 13 about a scan axis, as shown, thereby scanning the point light to produce linear light. The linear light comprises a plurality of rays of light (exemplary rays 15 being shown in the Figure), which are produced consecutively by the scan device 13 in scanning the point light and which fall on a line at the scanner 5, as shown.

The scan device 13 is positioned in the ophthalmoscope 1 such that it receives the point light from the source 11 substantially on its scan axis and is further positioned in the ophthalmoscope 1 such that its scan axis lies in a plane conjugate to a pupil 17 of the eye 9. Light incident on the scan axis of the scan device 13 will therefore be focussed at and pass through the eye pupil 17. The scan device 13 is further positioned in the ophthalmoscope 1 such that, in this embodiment, its scan axis lies at an angle of approximately 90 degrees to a scan axis of the scanner 5. It will be appreciated that in other embodiments, the scan axis of the scan device 13 could lie at a different angle to the scan axis of the scanner 5. In this embodiment, the scan axis of the scan device 13 is approximately horizontal and the scan axis of the scanner 5 is approximately vertical. It will be appreciated that in other embodiments, the scan axis of the scan device 13 could be approximately vertical and the scan axis of the scanner 5 could be approximately horizontal or the scan axes of the scan device 13 and the scanner 5 could have other orientations.

The scanner 5 comprises a plane mirror. The scanner 5 receives the linear light from the scan device 13 and is driven by a motor (not shown) to move it about its scan axis 19, as shown, to produce a 1D scan of the linear light (exemplary rays 21 of the 1D scan being shown in the Figure). The scanner 5 is positioned in the ophthalmoscope 1 such that it receives the linear light with a central axis of the light substantially coincidental with the scan axis 19. The scanner 5 has dimensions such that it receives substantially all of the linear light produced by the light system 3. The scanner 5 also has dimensions such that it receives substantially all of return light from the eye fundus. The scanner 5 is further positioned in the ophthalmoscope 1 such that the 1D scan 21 is transferred from the scanner 5 through a focal point at the eye pupil 17 and onto a fundus 23 of the eye 9.

The plane mirror scanner 5 has a substantially flat shape such that, in this embodiment, a scan direction of the 1D scan 21 of the linear light lies at an angle of approximately 90 degrees to the scan axis 19 of the scanner 5. It will be appreciated that in other embodiments, the scan direction of the 1D scan 21 could lie at a different angle to the scan axis 19 of the scanner 5. In this embodiment, the scan direction of the 1D scan 21 is approximately horizontal and the scan axis 19 of the scanner 5 is approximately vertical. It will be appreciated that in other embodiments, the scan direction of the 1D scan 21 could be approximately vertical and the scan axis 19 of the scanner 5 could be approximately horizontal or the scan direction of the 1D scan 21 and the scan axis 19 of the scanner 5 could have other orientations.

The scan transfer system 7 comprises a scan transfer component which is a reflective component in the form of a mirror. The scan transfer component has at least one focal point and the scan transfer system 7 is positioned in the ophthalmoscope 1 such that the eye pupil 17 is provided at the focal point of the component. The scan transfer system 7 is configured to transfer the 1D scan from the scanner 5 through the focal point at the eye pupil 17 and onto the eye fundus 23 by election of a shape of the scan transfer component. The scan transfer component has an aspherical shape and, in this embodiment, specifically has a shape of a section of a conical surface, such as any of parabolic, ellipsoidal, hyperboloid. The reflective component may have a shape described by one or more polynomial functions of two variables, for example, two variables describing substantially orthogonal axes of the reflective component.

The scan transfer component has a shape such that the at least some linear light from the scanner 5 is collimated at a location adjacent an outer surface of a cornea of the eye 9. The collimated light at the eye cornea is then focussed by the eye cornea and lens to give light having an optimised spread function at substantially each of a plurality of positions of a scan field on the eye fundus 23. The scan transfer component further has a shape such that return light from substantially each of the plurality of positions of the scan field on the eye fundus 23 has substantially similar focal properties and is substantially brought to a focus on a plane. A standard confocal aperture may then be used to optimise the signal-to-noise of the fundus return light.

The scan transfer component of the scan transfer system 7 has dimensions such that it receives substantially all of the 1D scan 21 from the scanner 5. The scan transfer component also has dimensions such that it receives substantially all of return light from the eye fundus 23. Thus the scan transfer components are able to collect light exiting the eye at wide and ultra wide angles, providing a wide and ultra wide ophthalmoscope.

Light from the light source 11 is thus transmitted by the scan device 13, the scanner 5 and the scan transfer system 7 of the ophthalmoscope 1 onto the fundus 23 of the eye 9. The scan device 13, the scanner 5 and the scan transfer system 7 act together to provide a 2D light scan at the fundus 23. Return light from the fundus 23 is transmitted back through the scan transfer system 7, the scanner 5 and the scan device 13 and is collected by a detector (not shown). Thus an image of the fundus 23 is created by the ophthalmoscope 1.

The components of the ophthalmoscope 1 effectively create an apparent point source of light at the pupil 17 of the eye 9. At the eye pupil 17 the light is focused onto an area smaller than the eye pupil for all angles of the scan of the fundus 23.

Figure 2:
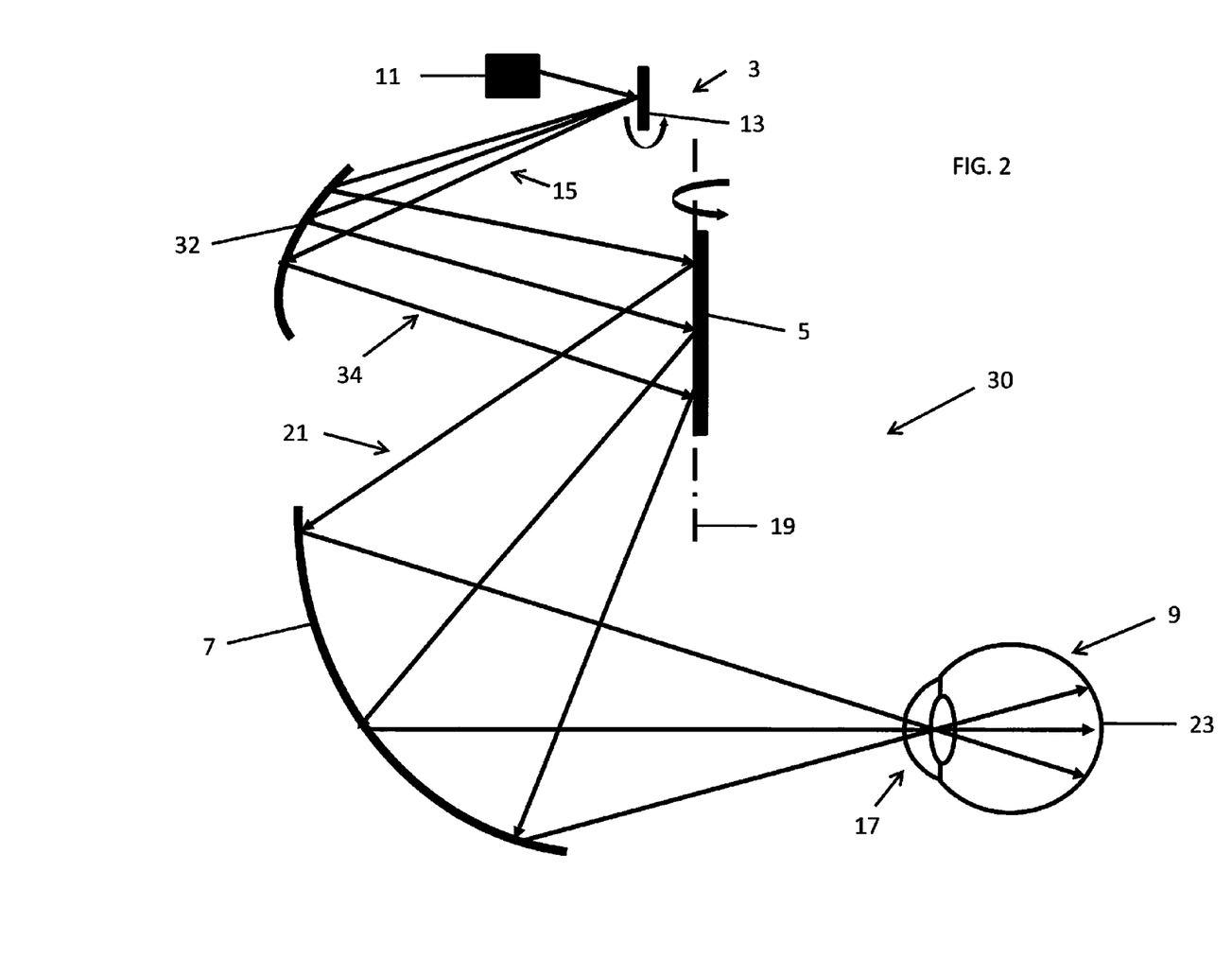
FIG. 2 is a schematic representation of a second embodiment of the ophthalmoscope according to the first aspect of the invention.

Referring to FIG. 2, a second embodiment of an ophthalmoscope according to the invention is shown. The ophthalmoscope of FIG. 2 has components in common with the ophthalmoscope of the first embodiment shown in FIG. 1 and like components have been denoted using the same reference numerals.

In FIG. 2, the ophthalmoscope 30 comprises a light system 3, a scanner 5 and a scan transfer system 7 and is used in scanning an eye 9. In addition, the ophthalmoscope 30 comprises a scan transfer device 32.

The scan transfer device 32 comprises an aspheric mirror and is positioned in the ophthalmoscope 30 between the light system 3 and the scanner 5 to relay the linear light from the light system 3 to the scanner 5. The linear light comprises a plurality of rays of light (exemplary rays 15 being shown in the Figure) which are produced consecutively by the scan device 13 in scanning the point light. The plurality of rays 15 are consecutively reflected from the second scan transfer device 32 and the reflected rays (exemplary rays 34 being shown in the Figure) fall on a line at the scanner 5, as shown. The reflected rays 34 are shown as mapping out a diverging scan of the linear light, but it will be appreciated that the reflected rays could map out a converging or collimated scan of the linear light.

The scan transfer device 32 has a shape and is positioned in the ophthalmoscope 30 such that aberration in the ophthalmoscope 30 is decreased.

The remaining components of the ophthalmoscope 30 of FIG. 2 function in the manner described with reference to the ophthalmoscope of FIG. 1. Light from the light source 11 is thus transmitted by the scan device 13, the scan transfer device 32, the scanner 5 and the scan transfer system 7 of the ophthalmoscope 30 onto the fundus 23 of the eye 9. The scan device 13, the scan transfer device 32, the scanner 5 and the scan transfer system 7 act together to provide a 2D light scan at the fundus 23. Return light from the fundus 23 is transmitted back through the scan transfer system 7, the scanner 5, the scan transfer device 32 and the scan device 13 and is collected by a detector (not shown). Thus an image of the fundus 23 is created by the ophthalmoscope 30.

Figure 3:
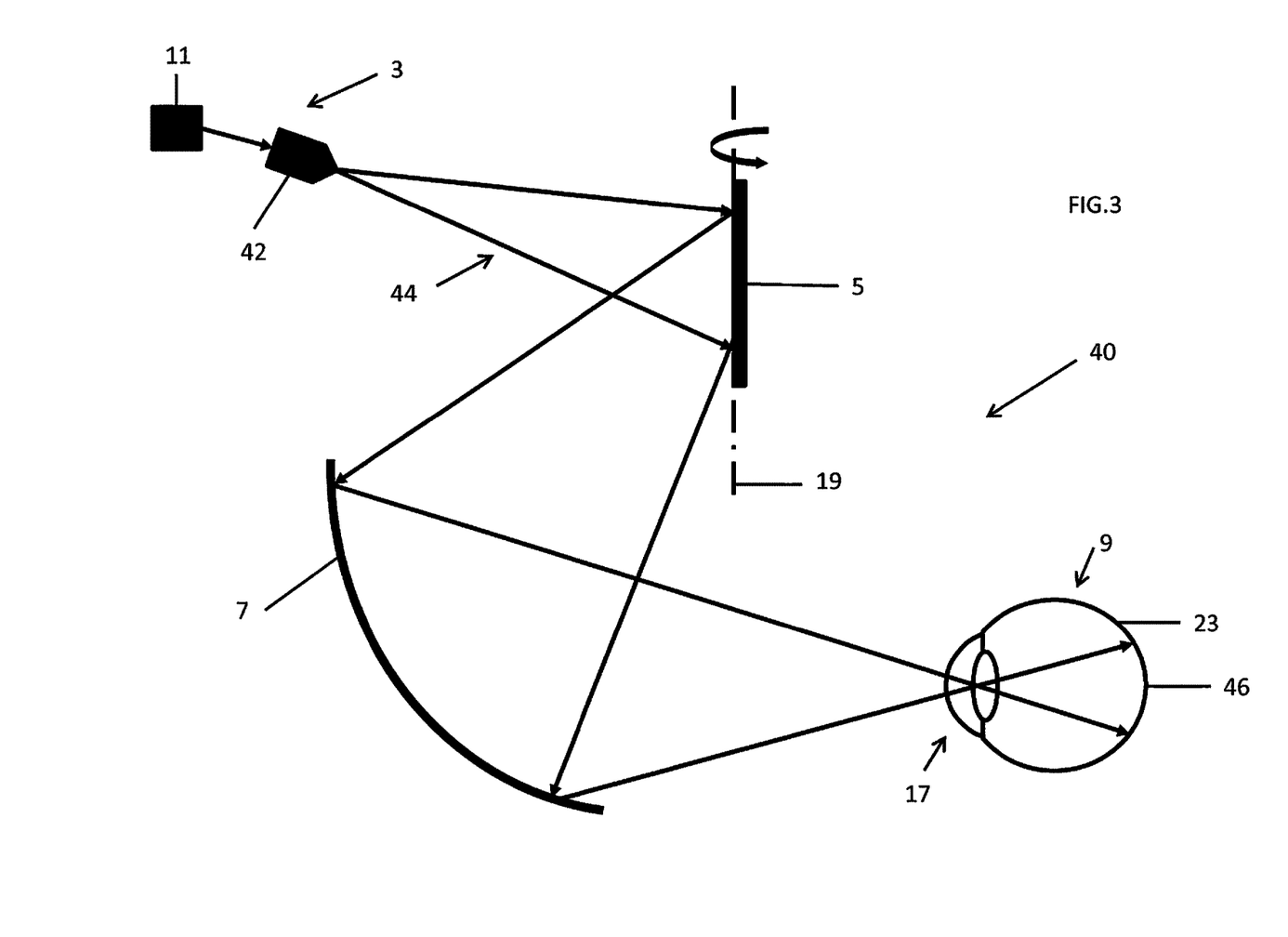
FIG. 3 is a schematic representation of a third embodiment of the ophthalmoscope according to the first aspect of the invention.

Referring to FIG. 3, a third embodiment of an ophthalmoscope according to the invention is shown. The ophthalmoscope of FIG. 3 has components in common with the ophthalmoscope of the first embodiment shown in FIG. 1 and like components have been denoted using the same reference numerals.

In FIG. 3, the ophthalmoscope 40 comprises a light system 3, a scanner 5 and a scan transfer system 7 and is used in scanning an eye 9.

The light system 3 comprises a point source of light 11, comprising a laser, and a light line generator 42. The light line generator 42 receives point light from the source 11 and produces linear light. The linear light comprises a plurality of rays of light which are produced simultaneously by the light line generator 42 and which form a fan of rays 44. The fan of rays 44 are incident on the scanner 5 and form a line of light at the scanner 5, as shown. The light line generator 42 is positioned in the ophthalmoscope 40 such that, in this embodiment, it produces a fan of rays 44 which is approximately parallel to the scan axis of the scanner 5. It will be appreciated that in other embodiments, the fan of rays 44 could lie at an angle to the scan axis of the scanner 5. In this embodiment, the fan of rays 44 and the scan axis of the scanner 5 are approximately vertical. It will be appreciated that in other embodiments, these could be approximately horizontal or could have other orientations.

The remaining components of the ophthalmoscope 40 of FIG. 3 function in the manner described with reference to the ophthalmoscope of FIG. 1. Light from the light line generator 42 is thus transmitted by the scanner 5 and the scan transfer system 7 of the ophthalmoscope 40 onto the fundus 23 of the eye 9. The light line generator 42, the scanner 5 and the scan transfer system 7 act together to provide a 2D light scan at the fundus 23, comprising a 1D scan of the 1D fan of rays 44 by the scanner 5. The light incident on the fundus 23 comprises an approximately vertical 1D fan of rays 46 which is scanned in an approximately horizontal scan direction over the fundus 23 to create the 2D light scan at the fundus 23. Return light from the fundus 23 is transmitted back through the scan transfer system 7 and the scanner 5 and is collected by a detector (not shown). Thus an image of the fundus 23 is created by the ophthalmoscope 40.

Figure 4:
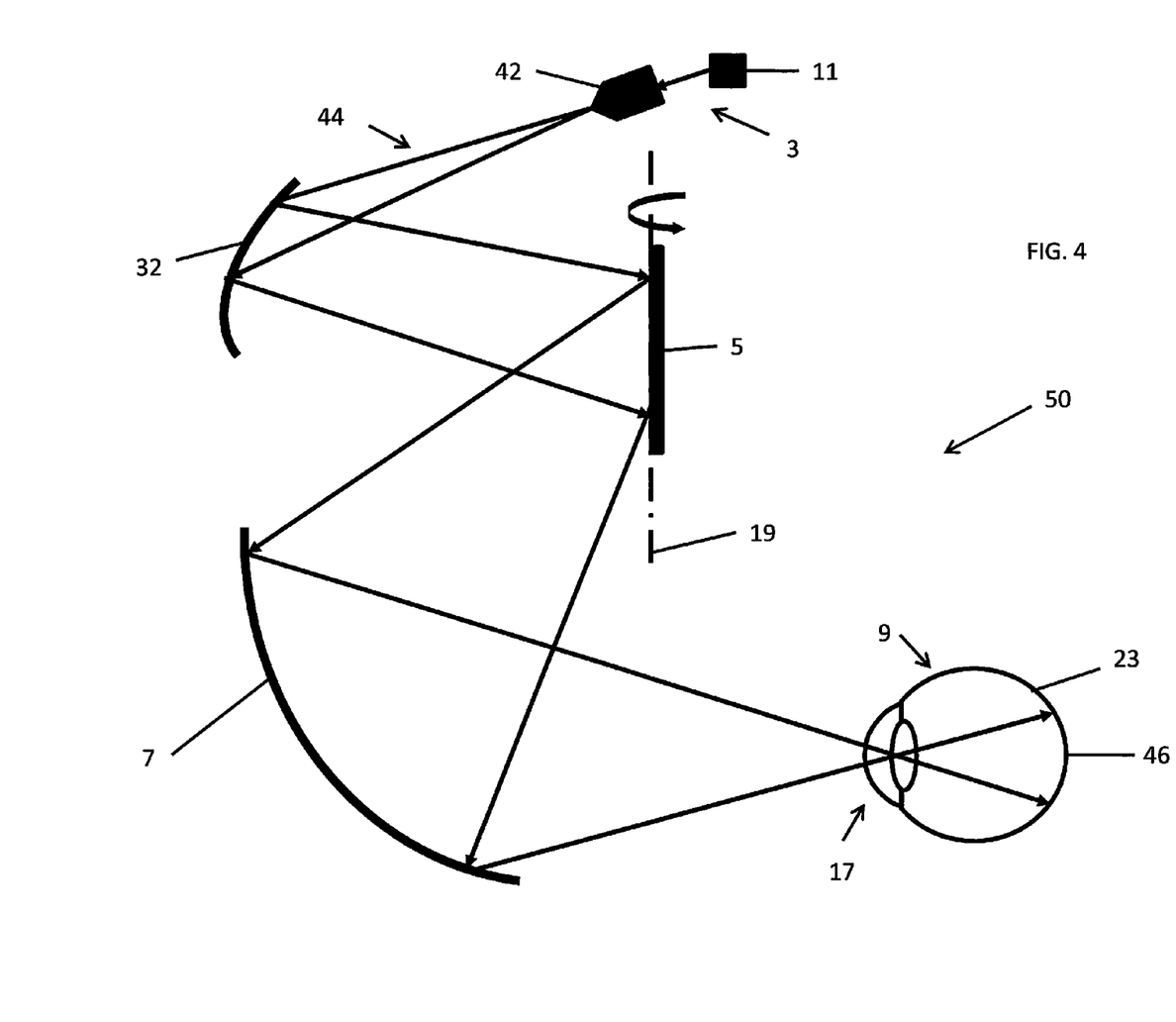
FIG. 4 is a schematic representation of a fourth embodiment of the ophthalmoscope according to the first aspect of the invention.

Referring to FIG. 4, a fourth embodiment of an ophthalmoscope according to the invention is shown. The ophthalmoscope of FIG. 4 has components in common with the ophthalmoscopes of the second and third embodiments shown in FIGS. 2 and 3 and like components have been denoted using the same reference numerals.

In FIG. 4, the ophthalmoscope 50 comprises a light system 3, a scanner 5 and a scan transfer system 7 and is used in scanning an eye 9. The light system 3 comprises a point source of light 11, comprising a laser, and a light line generator 42. In addition, the ophthalmoscope 50 comprises a scan transfer device 32, as described with reference to FIG. 2.

The remaining components of the ophthalmoscope 50 of FIG. 4 function in the manner described with reference to the ophthalmoscope of FIG. 3. Light from the light line generator 42 is thus transmitted by the scan transfer device 32, the scanner 5 and the scan transfer system 7 of the ophthalmoscope 50 onto the fundus 23 of the eye 9. The light line generator 42, the scan transfer device 32, the scanner 5 and the scan transfer system 7 act together to provide a 2D light scan at the fundus 23, comprising a 1D scan of the 1D fan of rays 44 by the scanner 5. The light incident on the fundus 23 comprises an approximately vertical 1D fan of rays 46 which is scanned in an approximately horizontal scan direction over the fundus 23 to create the 2D light scan at the fundus 23. Return light from the fundus 23 is transmitted back through the scan transfer system 7, the scanner 5 and the scan transfer device 32, and is collected by a detector (not shown). Thus an image of the fundus 23 is created by the ophthalmoscope 50.

It will be appreciated that further embodiments of the ophthalmoscope according to the first aspect of the invention can be provided in which the scan transfer system comprises a transmissive scan transfer component or the scan transfer system comprises a plurality of scan transfer components which may be reflective or transmissive components.

Figure 5:
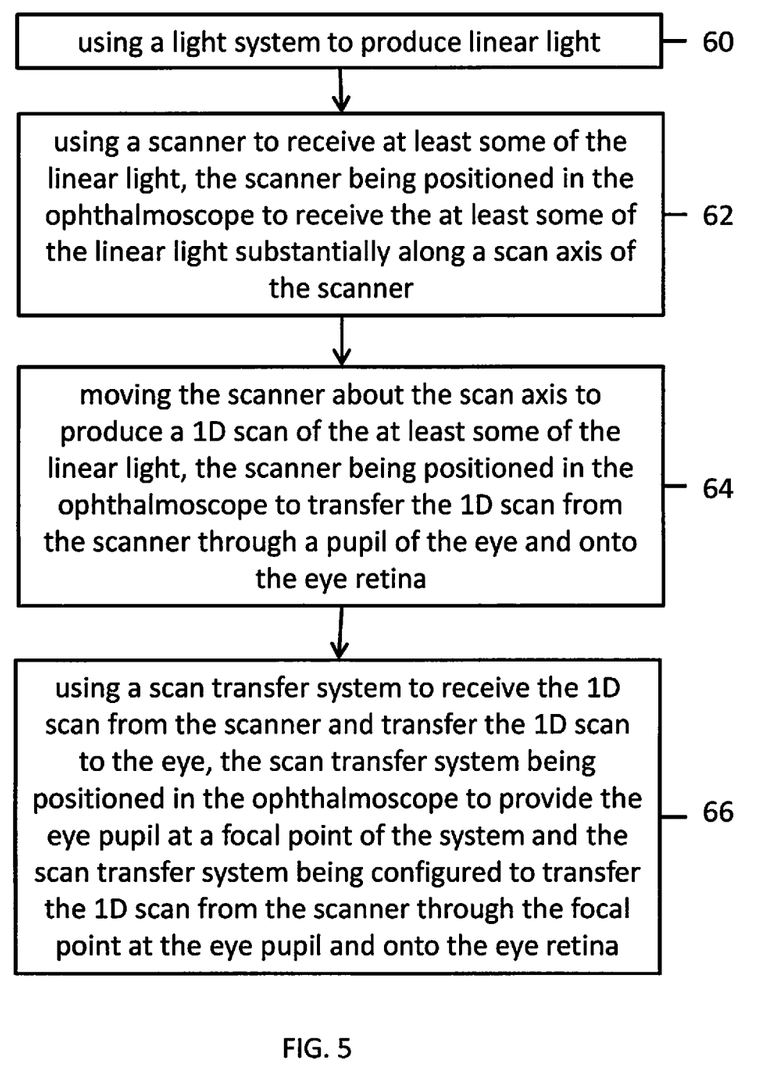
FIG. 5 is a flow chart representing the method according to the second aspect of the invention.

Referring to FIG. 5, a method of scanning a fundus of an eye is shown. The method comprises using a light system to produce linear light 60, using a scanner to receive at least some of the linear light 62, the scanner being positioned in the ophthalmoscope to receive the at least some of the linear light substantially along a scan axis of the scanner, moving the scanner about the scan axis to produce a 1D scan of the at least some of the linear light 64, the scanner being positioned in the ophthalmoscope to transfer the 1D scan from the scanner through a pupil of the eye and onto the eye fundus, and using a scan transfer system to receive the 1D scan from the scanner and transfer the 1D scan to the eye 66, the scan transfer system being positioned in the ophthalmoscope to provide the eye pupil at a focal point of the system and the scan transfer system being configured to transfer the 1D scan from the scanner through the focal point at the eye pupil and onto the eye fundus.

The invention claimed is:

1. An ophthalmoscope for scanning a fundus of an eye, comprising:
   a light system which produces linear light,
   a scanner which receives at least some of the linear light and is movable about a scan axis to produce a 1D scan of the at least some linear light, and
   a scan transfer system which receives the 1D scan from the scanner and transfers the 1D scan to the eye,
   a scan transfer device arranged to relay the at least some of the linear light from the light system to the scanner, the scan transfer device having a shape and being positioned in the ophthalmoscope so as to compensate for aberration in the ophthalmoscope;
   wherein the scanner is not positioned at a focal point of the scan transfer system and is positioned in the ophthalmoscope such that it receives the at least some of the linear light substantially along the scan axis, the scan transfer system is positioned in the ophthalmoscope such that a pupil of the eye is provided at a focal point of the scan transfer system, and the scanner is positioned in the ophthalmoscope and the scan transfer system is configured to transfer the 1D scan from the scanner through the focal point at the eye pupil and onto the eye fundus.

2. An ophthalmoscope according to claim 1 in which the scanner positioned in the ophthalmoscope such that it receives the at least some of the linear light with a central axis of the light substantially coincidental with the scan axis.

3. An ophthalmoscope according to claim 1 in which the scanner has a shape such that a scan direction of the 1D scan of the linear light lies at an angle to the scan axis of the scanner.

4. An ophthalmoscope according to claim 3 in which the scanner shape is substantially flat and the angle is approximately 90 degrees.

5. An ophthalmoscope according to claim 1 in which the scanner comprises a reflective element in the form of a mirror.

6. An ophthalmoscope according to claim 1 in which the scanner has dimensions such that it receives substantially all of the linear light produced by the light system.

7. An ophthalmoscope according to claim 1 in which the scanner has dimensions such that it receives substantially all of return light from the eye fundus.

8. An ophthalmoscope according to claim 1 in which the scan transfer system comprises a scan transfer component.

9. An ophthalmoscope according to claim 8 in which the scan transfer system is configured to transfer the 1D scan from the scanner through the focal point at the eye pupil and onto the eye fundus by election of a shape of the scan transfer component.

10. An ophthalmoscope according to claim 8 in which the scan transfer component has an aspherical shape.

11. An ophthalmoscope according to claim 10 in which the scan transfer component has a shape of a section of a conical surface.

12. An ophthalmoscope according to claim 11 in which the shape of the section of the conical surface is any of parabolic, ellipsoidal, hyperboloid.

13. An ophthalmoscope according to claim 8 in which the scan transfer component comprises a reflective component.

14. An ophthalmoscope according to claim 13 in which the reflective component has a shape described by one or more polynomial functions of two variables, for example, two variables describing substantially orthogonal axes of the reflective component.

15. An ophthalmoscope according to claim 13 in which the reflective component comprises a mirror.

16. An ophthalmoscope according to claim 8 in which the scan transfer component comprises a transmissive component.

17. An ophthalmoscope according to claim 16 in which the transmissive component comprise a lens.

18. An ophthalmoscope according to claim 8 in which the scan transfer component has a shape such that the least some linear light of the 1D scan is collimated at a location adjacent an outer surface of a cornea of the eye.

19. An ophthalmoscope according to claim 8 in which the scan transfer component has a shape such that return light from substantially each of the plurality of positions of the scan field on the eye fundus has substantially similar focal properties and is substantially brought to a focus on a plane.

20. An ophthalmoscope according to claim 8 in which the scan transfer component has dimensions such that it receives substantially all of the 1D scan from the scanner.

21. An ophthalmoscope according to claim 8 in which the scan transfer component has dimensions such that it receives substantially all of return light from the eye fundus.

22. An ophthalmoscope according to claim 1 in which the scan transfer system comprises a plurality of scan transfer components.

23. An ophthalmoscope according to claim 22 in which the scan transfer system is configured to transfer the 1D scan from the scanner through the focal point at the eye pupil and onto the eye fundus by election of shapes of the scan transfer components and positions of the scan transfer components.

24. An ophthalmoscope according to claim 1 in which the light system comprises a point source of light and a scan device which receives a point light and is movable about a scan axis to scan the point light to produce the linear light.

25. An ophthalmoscope according to claim 24 in which the linear light comprises a plurality of rays of light which are produced consecutively by the scan device scanning the point light and which fall on a line at the scanner.

26. An ophthalmoscope according to claim 24 in which the scan device is positioned in the ophthalmoscope such that it receives the point light substantially on the scan axis.

27. An ophthalmoscope according to claim 24 in which the scan device is positioned in the ophthalmoscope such that the scan axis lies in a plane conjugate to the eye pupil.

28. An ophthalmoscope according to claim 24 in which the scan device is positioned in the ophthalmoscope such that the scan axis of the scan device lies at an angle to the scan axis of the scanner.

29. An ophthalmoscope according to claim 24 in which the scan device comprises a plane mirror.

30. An ophthalmoscope according to claim 1 in which the light system comprises a point source of light and a light line generator to produce the linear light.

31. An ophthalmoscope according to claim 30 in which the linear light comprises a plurality of rays of light which are produced simultaneously by the light line generator and which form a line of light at the scanner.

32. An ophthalmoscope according to claim 1 in which the light system comprises a linear array of point sources of light to produce the linear light.

33. An ophthalmoscope according to claim 32 in which the linear light comprises a plurality of rays of light which are produced simultaneously by the point sources of light and which form a line of light at the scanner.

34. An ophthalmoscope according to claim 1 further comprising a scan transfer device.

35. An ophthalmoscope according to claim 34 in which the scan transfer device is positioned in the ophthalmoscope between the light system and the scanner to relay the at least some linear light from the light system to the scanner.

36. An ophthalmoscope according to claim 34 in which the scan transfer device comprises an aspheric mirror.

37. An ophthalmoscope according to claim 1 which is a wide field ophthalmoscope.

38. An ophthalmoscope according to claim 1 which is an ultra-wide field ophthalmoscope.

39. A method of scanning a fundus of an eye, comprising
using a light system to produce linear light,
using a scan transfer device to relay at least some of the linear light from the light system to a scanner, the scan transfer device having a shape and being positioned in a ophthalmoscope so as to compensate for aberration in the ophthalmoscope, using the scanner to receive the at least some of the linear light, the scanner being positioned in the ophthalmoscope to receive the at least some of the linear light substantially along a scan axis of the scanner, moving the scanner about the scan axis to produce a 1D scan of the at least some of the linear light, the scanner not being positioned at a focal point of a scan transfer system and being positioned in the ophthalmoscope to transfer the 1D scan from the scanner through a pupil of the eye and onto the eye fundus, and using a scan transfer system to receive the 1D scan from the scanner and transfer the 1D scan to the eye, the scan transfer system being positioned in the ophthalmoscope to provide the eye pupil at a focal point of the system and the scan transfer system being configured to transfer the 1D scan from the scanner through the focal point at the eye pupil and onto the eye fundus.

\* \* \* \* \*